United States Patent [19]

Gumprecht et al.

[11] 4,186,188

[45] Jan. 29, 1980

[54] TREATING HAIR WITH COSMETIC FORMULATIONS CONTAINING POLYPEPTIDES

[76] Inventors: Janet A. Gumprecht, Marina Del Rey, Calif.

[73] Assignee: Redken Laboratories, Inc., Canoga Park, Calif.

[21] Appl. No.: 845,057

[22] Filed: Oct. 25, 1977

Related U.S. Application Data

[63] Continuation-in-part of Ser. No. 635,309, Nov. 26, 1975, abandoned.

[51] Int. Cl.² ............................................. A61K 7/06
[52] U.S. Cl. ................................ 424/70; 260/112 R; 260/117; 260/119; 260/121; 260/123.5; 260/123; 260/123.7; 424/DIG. 2; 424/359
[58] Field of Search .................. 424/DIG. 2, 70, 359; 260/112 G, 112 R, 117, 119, 121, 123.7, 123, 123.5

[56] References Cited

U.S. PATENT DOCUMENTS

| | | | |
|---|---|---|---|
| 3,061,512 | 10/1962 | Anderson et al. | 424/180 |
| 3,558,770 | 1/1971 | Gordon et al. | 424/80 |
| 3,683,939 | 8/1972 | Johnsen et al. | 424/70 X |
| 3,738,913 | 6/1973 | Johnsen et al. | 424/70 X |
| 3,751,564 | 8/1973 | Eckardt et al. | 424/70 |
| 3,904,748 | 9/1975 | Eckert et al. | 424/70 |
| 3,954,725 | 5/1976 | Johnsen et al. | 424/70 X |

Primary Examiner—James O. Thomas, Jr.
Assistant Examiner—Vera C. Clarke
Attorney, Agent, or Firm—Christie, Parker & Hale

[57] ABSTRACT

Polypeptides with sterically unhindered positive charges can be incorporated into a cosmetic formulation for human hair, skin and nails. The polypeptides, which can be prepared by trypsin catalyzed hydrolysis of proteins, have the formula:

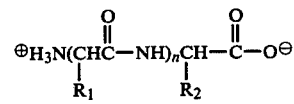

wherein n is an integer sufficient to provide a molecular weight of the polypeptide of from about 200 to about 2,000 each $R_1$ is independently a side group attached to the alpha carbon of a naturally occurring amino acid; and $R_2$ is selected from the group consisting of:

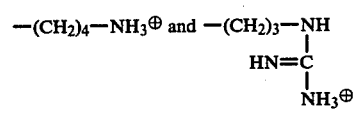

6 Claims, 1 Drawing Figure

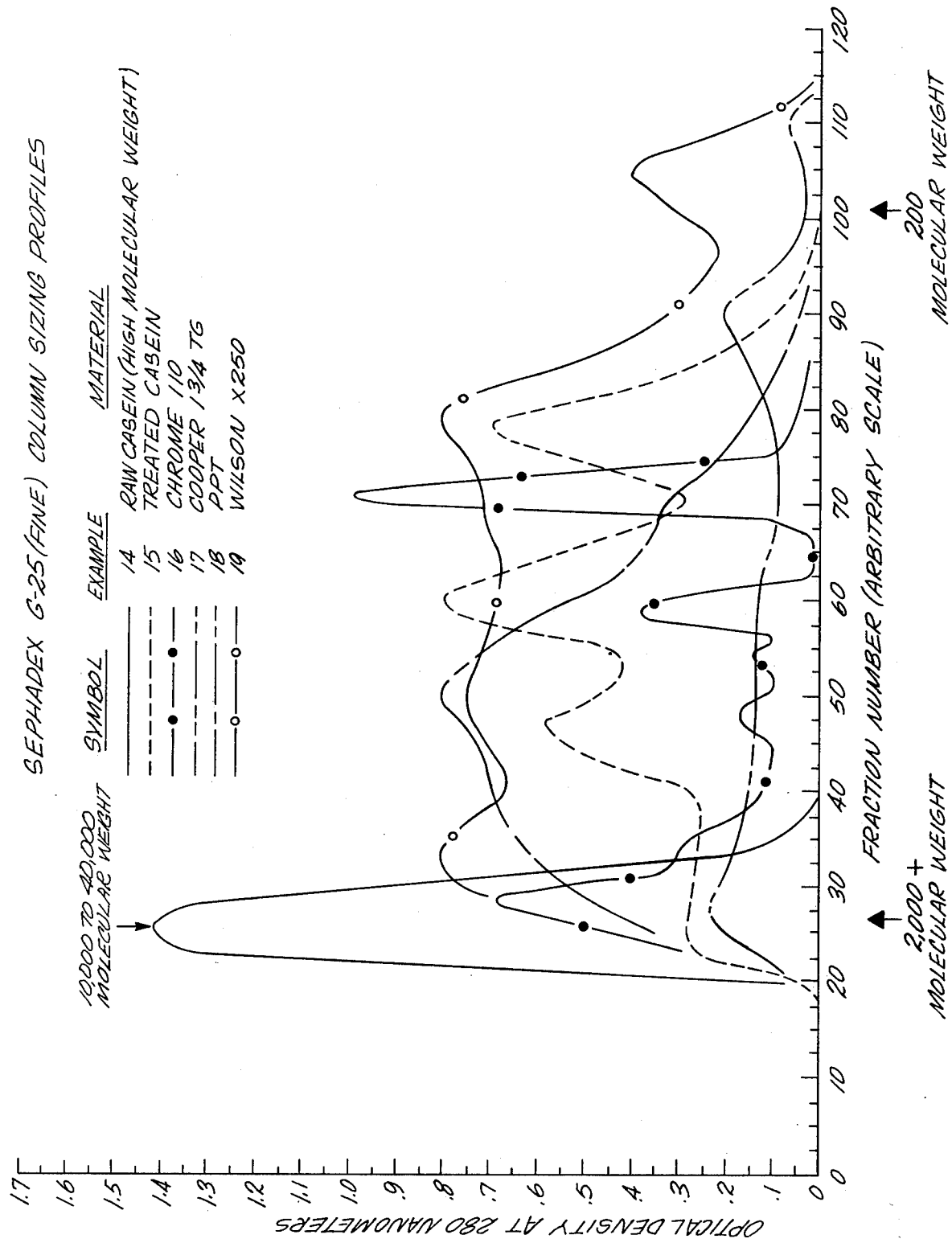

TREATING HAIR WITH COSMETIC FORMULATIONS CONTAINING POLYPEPTIDES

CROSS-REFERENCE

This application is a Continuation-in-part of copending and coassigned U.S. patent application Ser. No. 635,309 filed on Nov. 26, 1975, now abandoned, which application is incorporated herein by this reference.

BACKGROUND OF THE INVENTION

The external keratin tissue, which represents the protective covering of the human body, encompasses hair, skin and nails. It is well known that cosmetic treatments alter the character of keratin, and in particular, bleaching, straightening, toning, tinting and permanent waving of the hair exhibit the strongest influence on keratin proteins. Mechanical actions such as combing, brushing and the use of curling irons may also alter the character of hair keratin. Bleaching and tinting, both of which are oxidative chemical processes, convert a substantial amount of cystine, a sulfur containing amino acid, which is a component of keratin, to various oxidative products, cysteic acid being the most prominent moiety produced. In a conventional two step permanent waving process the disulfide bond of cystine is first reduced to two sulfhydryl groups, the cystine being converted to two cysteine moieties. In the second step the sulfhydryl groups are oxidized to convert the sulfhydryl groups back to the cystine disulfide bond.

However, this oxidation reaction generally does not completely convert the sulfhydryl groups back to the cystine disulfide bond. Instead, many of the sulfhydryl groups are oxidized to produce anionic $SO_3^\ominus$ groups which are present in cysteic acid. Since the disulfide bonds contribute to the strength of hair, hair treated by permanent waving and other cosmetic treatments exhibits a loss of strength of the hair.

Keratinous tissues are normally acidic, having isoelectric points on the acid side of the pH scale. The combination of the normal acidity of hair and the acidic end groups resulting from oxidative cosmetic chemical processes decreases the isoelectric point of hair and makes it even more acidic.

Therefore, hair treated by bleaching, tinting, or permanent waving exhibits a loss of disulfide bonds and increased acidity which are manifested by a loss of the hair's inherent strength and manageability. Thus hair subjected to cosmetic treatment often is in need of additives to restore the hair to its natural qualities and to improve the damaged condition of the hair.

A well known method used to improve the cosmetic feel and appearance of various keratinous materials, especially damaged human hair, skin and nails, is to treat the hair with compositions containing polypeptides. Polypeptides have proven to be especially useful in improving the cosmetic feel and appearance of hair damaged by bleaching processes, tinting and permanent waving.

Polypeptides can be produced by subjecting naturally occurring proteins to acid, base and/or enzymatic hydrolysis. For example, U.S. Pat. No. 3,683,939 describes compositions for treating hair where the compositions contain polypeptides of molecular weight of from 500 to 1500 prepared by partially hydrolyzing collagen by the application of heat and pressure, recovering anions from the formed protein hydrolysate, and completing the hydrolysis with a proteolytic enzyme.

A problem with these compositions prepared by conventional acid, base, and enzymatic hydrolysis methods is that they lack uniformity and consistency for two reasons. First, the quality of the product polypeptides is dependent upon minor variations in such variables as the source of the collagen, the pressure, pH, and length of time of the hydrolysis, and the choice of enzyme for the enzymatic hydrolysis. Second, it is impossible to control which peptide linkages of the collagen are hydrolyzed during the preparation of the polypeptides. Thus different production batches of these polypeptides have different end groups with different chemical characteristics and therefore affect hair differently. Also, these polypeptides generally lack the positive charge necessary to combine with the acidic end groups of hair which have been produced by the more radical salon treatments.

Therefore, it is desirable to produce cosmetic compositions for keratinous tissue containing reproducible polypeptides which are beneficial to the cosmetic appeal, manageability, body and sheen of damaged keratinous tissues. These polypeptides should be derived from proteins so that the positive charges of proteins would be available to neutralize the acidity of damaged hair. Also, these polypeptides should have positive groups located at the extremities of the molecule so that they would be capable of forming ionic bridges between keratin protein chains. In addition, the polypeptides should be of an optimal molecular size to make penetration into the hair shaft possible, and they should be able to be economically manufactured by reproducible means.

SUMMARY OF THE INVENTION

It has now been found that certain cosmetic preparations for treatment of keratinous tissue containing charged polypeptides have the above features. Specifically, these cosmetic preparations comprise aqueous solutions having a pH from about 4 to about 9, which solutions contain polypeptides, including a cosmetically effective amount of polypeptides having two sterically unhindered positive charges, the charged polypeptides having the formula:

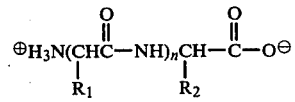

wherein n is an integer sufficient to provide a molecular weight of the polypeptides of from about 200 to about 2000; each $R_1$ is independently a side group attached to the alpha carbon of a naturally occurring amino acid; and $R_2$ is selected from the group consisting of:

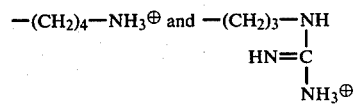

which are the side groups attached to the alpha carbon of the amino acids lysine and arginine, respectively. At least 16 mole% of the polypeptides in the aqueous solution are these charged polypeptides. These charged polypeptides can be prepared by the hydrolysis of selected proteins containing from 12 to 70% by weight arginine and lysine in combination.

When the cosmetic preparation is used for treating hair, the aqueous solution preferably has a pH from about 4 to about 7, and more preferably from about 4 to about 5.

Keratinous tissue treated with cosmetic preparations embodying features of this invention exhibits cosmetic characteristics including better texture than keratinous tissue treated with conventional cosmetic formulations. In particular, hair treated with cosmetic preparations embodying features of this invention exhibits better manageability, body and sheen than hair treated with conventional cosmetic formulations.

DRAWINGS

These and other features, aspects and advantages of the present invention will become more apparent from the following detailed description, examples, appended claims, and accompanying drawing which shows the molecular weight distribution of polypeptides in various aqueous solutions.

DESCRIPTION

My invention is for cosmetic preparations useful for treating keratinous tissue, particularly for treating hair, and methods for using these preparations. These preparations comprise an aqueous solution having a pH from about 4 to about 9 containing polypeptides, including a cosmetically effective amount of polypeptides having two sterically unhindered positive charges referred to herein as the "charged" polypeptides, the charged polypeptides having the formula:

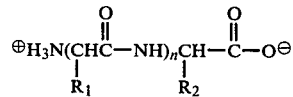

wherein n is an integer sufficient to provide a molecular weight of the polypeptide from about 200 to about 2000; each $R_1$ is independently a side group attached to the alpha carbon of a naturally occurring amino acid; and $R_2$ is selected from the group consisting of:

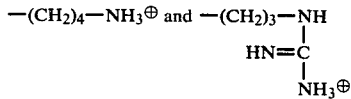

At least 16 mole percent of the polypeptides in the aqueous solution are charged polypeptides.

To provide a molecular weight for the polypeptides of from about 200 to about 2000, "n" can be an integer of from about 2 to about 30. To provide a molecular weight for the polypeptide of from about 700 to about 1600, "n" can be an integer of from about 4 to about 25. The molecular weight of the polypeptide depends upon not only n, but also upon $R_1$ and $R_2$. For example, when $R_2$ of the side chain attached to the alpha carbon of lysine and all the $R_1$'s are —$CH_3$, the side chain attached to the alpha carbon of the amino acid alanine, an n of about 12 gives a polypeptide with a molecular weight of about 1000 and an n of about 21 gives a polypeptide with molecular weight of about 1500. If all the $R_1$'s are changed to $(CH_3)_2CH_1$—, the side group attached to the alpha carbon of valine, then an n of 12 gives a molecular weight of about 1335. Thus, n is a function of the molecular weight of the product, and the choice of the side groups $R_1$ and $R_2$.

$R_1$ represents side groups attached to the alpha carbon of naturally occuring amino acids. Since each $R_1$ is independent of the other $R_1$'s in each polypeptide, succeeding $R_1$'s in a polypeptide can be the same or different. The $R_1$ side groups include hydrogen, hydrocarbons, and hydrocarbons combined with inorganic elements. Typical $R_1$ side groups include H, $(CH_3)_2CHCH_2$—, $CH_3SCH_2CH_2$—, $CH_3CHOH$—, $(CH_3)_2CH$—,

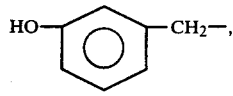

and the like, the side groups attached to the alpha carbon of the amino acids glycine, leucine, methionine, threonine, valine, and tyrosine, respectively.

The polypeptides with two sterically unhindered positive charges used in the cosmetic preparations of this invention can be produced by the trypsin catalyzed hydrolysis of a protein containing residues of either arginine or lysine, or both. The enzyme trypsin attacks proteins at the carboxy end of peptide linkages formed by these two amino acids, thereby forming a sterically unhindered positively charged $NH_3^\oplus$ group at one end of the polypeptide. The second positive charge occurs on the $R_2$ side group which also is sterically unhindered.

For a given known protein, substantially reproducible polypeptides having two sterically unhindered positive charges are produced by trypsin catalyzed hydrolysis. By knowing the frequency and location of lysine and arginine in the protein chain, it is possible to predict the structure of the polypeptides produced by tryptic hydrolysis. Thus polypeptides having two sterically unhindered positive charges and a predictable molecular size, structure and reactivity are produced. Also, polypeptides having variations in molecular size and structure can be obtained by using a mixture of proteins as the source material. This is unlike conventional acid, base and high temperature protein hydrolysis techniques, used either alone or in combination with enzymatic hydrolysis, where the structure of the product polypeptides is not reproducible and the polypeptides usually do not have sterically unhindered positive charges available at both ends of the molecule.

The proteins which may be used in the preparation of charged polypeptides from trypsin catalyzed hydrolysis cover a wide range. These proteins can be classified according to their biological function, and include structural proteins such as collagen, keratin, fiberoin, elastin, sclerotin, and the like; storage proteins such as ovalbumin, casein, ferritin, gliadin, zein, and the like; transport proteins such as serum albumin, hemoglobin, $B_1$-lipoprotein, ceruloplasmin, and the like; and contractile proteins such as myosin, actin, dyneim, and the like, and mixtures thereof.

Proteins useful with this invention encompass both unconjugated and conjugated proteins such as metalloproteins, nucleoproteins, phosphoproteins, glycoproteins and lipoproteins. These proteins are obtainable from many sources, including animals, plants, poultry, dairy by-products, molds, fungus, yeast, and bacteria. Typical of the proteins useful for producing charged peptides include casein, collagen, feather keratin, and soy protein.

Not only may naturally occurring proteins be used to produce charged polypeptides, but also synthetic proteins containing lysine or arginine, or both, may be used. For example, polylysine and polyarginine may be used to produce charged peptides useful for the cosmetic preparations of this invention.

Mixtures of any of the above proteins may also be used.

To increase the weight percent charged polypeptides in the cosmetic preparation, the proteinaceous starting material used for preparing the polypeptides can be selected to maximize the amount of polypeptides having lysine and arginine end groups in the cosmetic preparation.

When the proteinaceous starting material contains more than about 70% by weight arginine and lysine in combination, conventional hydrolysis can yield polypeptides containing a high percentage of charged polypeptides having two sterically unhindered positive charges. Therefore, trypsin catalyzed hydrolysis is used primarily with proteinaceous starting materials containing only up to about 70% by weight arginine and lysine in combination.

There are numerous proteinaceous starting materials which contain from about 12% to about 70% by weight, and preferably at least 15% by weight, lysine and arginine in combination. Such proteinaceous starting materials containing from about 12 to about 70% by weight arginine and lysine include salmine, histones, and myoglobin, but do not include collagen.

The particular source of the proteins used for producing the charged polypeptides is not important. What is important are the structure and the percentage of lysine and arginine amino acids constituting the protein source.

The method of using the cosmetic preparations of this invention comprises contacting the keratinous tissue to be treated with the cosmetic preparation. Of the polypeptides in the aqueous solution of the cosmetic preparation, at least 16 mole% of the polypeptides are charged polypeptides having two sterically unhindered positive charges. For example, hair can be treated by contacting the hair with conditioning lotion which comprises from about 3 to about 35% by weight of polypeptides, of which polypeptides at least about 16 mole percent are charged polypeptides. A shampoo preferably contains from about 0.5 to about 5% by weight polypeptides, including at least about 16 mole percent charged polypeptides.

The molecular weight of the starting protein may affect the generation of the specific polypeptides of this invention since a combination of random and specific hydrolysis steps may be necessary to produce polypeptides of the desired molecular weight range. Specific hydrolysis methods utilize enzymes which preferentially break the native protein chain at certain amino acid sites. In the case of the desired polypeptides, the enzyme trypsin cleaves the native protein chain to generate lysine or arginine at the C-terminal of the polypeptide fragment, thus producing the desirable polypeptide. Any random step may necessarily introduce random polypeptides which do not have the specific lysine and/or arginine C-terminal of the desired polypeptides of this invention. The higher the proportion of lysine and/or arginine in the native protein, the less likely the production of undesirable polypeptides since the results of random and specific hydrolyses approach one another for lysine or arginine rich proteins.

This in turn could be related to the degree or hydrolysis. A higher molecular weight protein must be hydrolyzed to a greater degree to produce the molecular weight range of the desired polypeptides. Greater degree of hydrolysis increases the chance of producing random polypeptides not possessing the desired lysine or argininee C-terminal.

While it is recognized that all such factors may play a part in the production of the desired polypeptides, the overriding factor is the composition, not the biological class of protein. By selecting the proper protein or mixtures thereof, the total amount of lysine and arginine C-terminal polypeptides can be controlled, as well as the ratio of one type to another. Thus, the mole percent lysine and/or arginine in the starting protein, coupled with the degree of hydrolysis necessary to provide polypeptides of the desired molecular weight, dictates whether random or specific hydrolysis methods are used.

When the charged polypeptides are prepared by trypsin catalyzed hydrolysis of proteins, it is inevitable that polypeptides not having two sterically unhindered positive charges and not produced by the trypsin catalyzed hydrolysis of the protein are contained in the aqueous solution whenever a naturally occurring protein is hydrolyzed. The source of these polypeptides without two sterically unhindered positive charges are two-fold. First, the proteinaceous raw material necessarily has an amino acid end group which usually is not lysine or arginine. Thus, no matter how many lysine or arginine amino acids are contained in the protein, it is inevitable that at least one polypeptide resulting from the hydrolysis of this protein will not conform to the formula presented above.

The second source of non-conforming polypeptides results from the steps used to extract the protein before it can be subjected to trypsin catalyzed hydrolysis. For example, collagen may be obtained from pigs' feet by hot water extraction techniques. It is inevitable that during this hot water extraction, some hydrolysis of the protein contained in the collagen results.

Thus, the cosmetic preparations of this invention comprises an aqueous solution of polypeptides of which at least 16 mole percent are charged polypeptides having two sterically unhindered positive charges.

Exemplary of the method used for producing polypeptides of the invention is the enzymatic hydrolysis of gelatin. This reaction preferably takes place at basic conditions with pH from about 8 to about 8.5. Preferably the temperature of the gelatin is elevated to increase the rate of hydrolysis, but temperatures less than about 180° F. are used to prevent denaturization of the enzyme. The reaction is usually taken to completion. The degree of completion is checked against known molecular weight standards using gel filtration chromatography. If it is necessary to stop the reaction before completion, acid is added to the solution or the solution is heated to about 180° F. to denature the trypsin.

Although not bound by theory, it is believed that the cosmetic preparations of this invention improve the cosmetic quality of hair by balancing out the excess of anionic charges resulting from cosmetic treatment. This balancing results from the excess number of positively charged groups which occur on the charged peptides which are contained in the cosmetic preparation of this invention. Because the aqueous solutions used for the cosmetic preparations of this invention have a pH from about 4 to about 9, there are protons available in the solution to provide a net positive charge on the polypeptides. This excess of positive charges occurs on the $R_2$ side group, which is a proton acceptor group, either lysine or arginine.

It is preferred that the cosmetic formulations of this invention be acidic because the excess positive charges on the charged polypeptides are present when the cosmetic preparation is acidic. In addition, the charged polypeptides are partially insoluble at a pH less than 4 and greater than 9. The formulations of this invention are functional over a pH range of from about 4 to about 9. A low pH is preferable because as the solution becomes more basic, fewer positive charges are available for the polypeptides. However, at a pH less than about 4 there is a risk of damage to human skin, and a portion of the charged polypeptides are insoluble. In the cosmetic treatment of chemically damaged hair it is preferred that the pH be from about 4 to about 7, and more preferably from about 4 to about 5.

These charged polypeptides having two sterically unhindered positive charge groups restructure keratinous tissue such as hair by having the ability to form cross salt linkages where cystine cross-linkages have been destoyed due to chemical attack of the disulfide bond. These cross salt linkages result in a three dimensional strengthening which occurs because the sterically unhindered extremities off the charged polypeptides in the cosmetic formulations of this invention i.e., the $R_2$ side group and the $NH_3^\oplus$ groups, are positively charged, and are available for maximum efficiency of bonding to weakened hair.

Although not bound by theory, it is believed that hair is oxidized by salon treatment of hair and then restructured by the cosmetic formulations of this invention as follows:

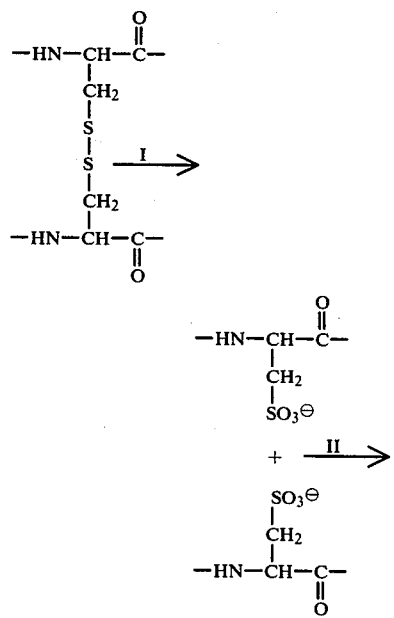

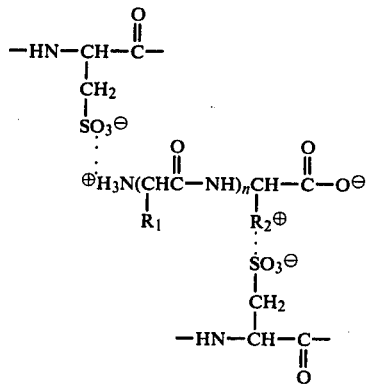

In step I, the disulfide bond of keratinous cystine is reduced to sulfhydryl groups and then oxidized to yield cysteic acid. In step II the sterically unhindered positively charged end groups of the polypeptides of this invention bond to the anionic $SO_3^\ominus$ end groups of cysteic acid, thereby three dimensionally strengthening the treated keratinous tissue.

These and other advantages of cosmetic preparations of this invention are shown by the following examples:

Controls 1A–8L

Eight subjects (#1–#8) each provided twelve control swatches of hair for twelve different control treatments (A–K) for a total of 96 control swatches. Each swatch was identified with a number and a letter, i.e., 1A, 1B, 1C . . . 8J, 8K. The number represented the number of the subject and the letter represented the treatment.

The case histories of subjects 1, 3, 4, 7 and 8 was as follows:

Case No.

1 Age 23, F, Caucasian with light brown hair of medium texture. Wavy, thick, no tinting, no straightening, normal scalp. Permanent wave in 1963, no bleaching.

3 Age 19, F, Caucasian with black, dull, thick, wavy, long hair. No tint or bleach, no permanent wave, no chemical straightening.

4. Age 22, F, Caucasian, no tinting or bleaching, no chemical straightening, no permanent wave.

7. F, Caucasian, brown, oily, straight, medium texture, short hair.

8. Breaking, thin, fine, brown hair. Tinted hair, not bleached. Short hair, no chemical straightening, no permanent wave.

The case histories of subjects 2, 5 and 6 were not available.

The swatches were treated as follows:

| Treatment | |
|---|---|
| No treatment | A |
| | B |

Shampooed only. The operator wore rubber gloves and used tap water for both the shampooing and rinsing steps. Swatches of subjects #1, #2 and #3 were shampooed with deep cleansing anionic shampoo having a pH of from 5 to 6. The swatches of subjects #4, #5 and #6 were shampooed in a gentle conditioning anionic shampoo having a pH range of from 4.5 to 5.5. The swatches of subjects #7 and #8 were shampooed 3 times with the conditioning shampoo and the third sudsing was left in the swatch. Neither shampoo left a filmy residue in the hair.

C-K

The swatches for treatments C-K were shampooed as in treatment B, and then an aqueous solution, as listed in Table 1, was applied with a tint brush, left on for 20 minutes, and then rinsed away with tap water.

TABLE 1

| Control Treatment | Solution[1] |
|---|---|
| C | 15% carnapro enzymatic hydrolysate, pH of 4.0 |
| D | 20% carnapro enzymatic hydrolysate |
| E | 15% casein enzymatic hydrolysate, pH of 4.0 |
| F | 20% casein enzymatic hydrolysate, pH of 4.0 |
| G | 15% collagen enzymatic hydrolysate |
| H | 20% collagen enzymatic hydrolysate |
| I | 10% feather hydrolysate |
| J | Climatress[2] |
| K | P.P.T. "S-77"[3] |

| Example Treatment | Solution |
|---|---|
| L | 15% tryptic hydrolysate |
| M | 20% tryptic hydrolysate |

Notes:
[1] all % are by weight
[2] Climatress is the trademark for a hair conditioner product containing acid hydrolyzed collagen hydrolysate marketed by Redken Laboratories, Inc., of Canoga Park, California.
[3] PPT "S-77" is the trademark for a hair conditioner product containing acid hydrolyzed polypeptides marketed by Redken Laboratories, Inc., of Canoga Park, California.

Each swatch was evaluated on a scale of 1 to 5 for manageability, body and sheen by two skilled cosmetologists, according to the following standards:

Manageability
1. Excellent—excellent to style, extremely easy to comb, not flyaway.
2. Good—easy to comb, easy to style, manageable.
3. Average—slightly flyaway.
4. Fair—fair drag, slightly wiry.
5. Poor—flyaway, bad drag, wiry, matted.

Body
1. Excellent—beautiful, great body.
2. Good—good feel, good bounce.
3. Average—fairly good, damp, fairly smooth, nice body, silky, soft.
4. Fair—fair bounce, slightly dry.
5. Poor—dry, stringy, oily, limp, rough.

Sheen
1. Excellent—beautiful, excellent sheen.
2. Good—good, nice.
3. Average—nice.
4. Fair—slight sheen, slightly gummy.
5. Poor—dull, drab, gummy.

The results of the cosmetic analysis of the treated control swatches are presented in Table 2. In this table the evaluation of each cosmetologist is presented with the first, second, and third numbers representing the cosmetologist's analysis of manageability, body, and sheen respectively. Thus, a rating of 1, 2, 4 indicates excellent manageability, good body, and fair sheen. The lower the rating number, the better the hair quality. The averages for the treatments were computed and also are presented in Table 2.

Examples 1L–8M

The eight subjects (#1–#8) who provided control swatches 1A–8K each provided two swatches of hair for treatments with solutions prepared according to this invention.

Each swatch was shampooed as in treatment B, and then an aqueous solution as listed in Table 1 was applied with a tint brush, left on for 20 minutes, and then rinsed away with tap water.

The results of the cosmetic analysis of the treated example swatches are presented in Table 2 using the same format used for the control swatches.

Comparison of the results for the example swatches with the results for the control swatches, as summarized in Table 2, clearly shows that cosmetic preparations embodying features of this invention impart superior manageability, body, and sheen to hair, as compared to conventional hair preparations.

TABLE 2

| | | EXAMPLES | | | | | | CONTROLS | | | | | | | | | |
|---|---|---|---|---|---|---|---|---|---|---|---|---|---|---|---|---|---|
| | | L | | | M | | | A | | | B | | | C | | | D |
| SUBJECT | 1 | 2.5 | 1 | 3 | 2.5 | 2 | 2 | 3 | 4.5 | 3 | 3 | 4 | 2.5 | 4 | 3 | 1 | 2 | 3 | 1 |
| | | — | 1.5 | 2 | — | 2 | 2 | — | 4 | 2.5 | — | 2.5 | 2.5 | — | 2 | 2 | — | 2 | 4 |
| | 2 | 3 | 3 | 3 | 2.5 | 2 | 1 | 2 | 2 | 3 | 3 | — | 2 | 2 | 1 | 1 | 2 | 3 | 1 |
| | | — | 3 | 3 | — | 3 | 2.5 | — | 2.5 | 2.5 | — | 2 | 2.5 | — | 3 | 3 | — | 2 | 2.5 |
| | 3 | 2 | 3 | 1 | 3 | 1 | 3 | 4.5 | 2.5 | 2 | 2 | 1 | 2 | 2 | 1 | 2 | 1 | 1 |
| | | — | 2 | 1.5 | — | 2 | 2 | — | 4 | 2.5 | 4 | 4 | 4 | — | 2 | 2.5 | — | 2 | 2 |
| | 4 | 2.5 | 2.5 | 1 | 2.5 | 2.5 | 3 | 5 | 4 | 3 | 5 | 2.5 | 1 | 3 | — | 1 | 3 | — | 1 |
| | | — | 2 | 1.5 | — | 2.5 | 2 | — | 3 | 3 | — | 2 | 1.5 | — | — | 4 | — | 2 | 2 |
| | 5 | *2 | 3 | 1 | *2 | 2.5 | 1 | 5 | 5 | 3 | 3 | 3.5 | 1 | 3 | 3 | 1 | 3 | 3 | — |
| | | — | 2 | 2 | — | 2 | 2 | — | 5 | 2.5 | — | — | 2 | — | 2 | 4 | — | 3 | 2 |
| | 6 | 1.5 | 1 | 2 | 1 | 3 | 2.5 | 3.5 | 3 | 5 | 3 | 1 | — | 3.5 | 1 | 2 | 1 | 1 | |
| | | — | 1.5 | 2 | — | 2 | 3 | — | 2 | 2.5 | — | 2 | 3 | — | 2 | 4 | — | 2 | 4 |
| | 7 | 2 | 2.5 | 1 | 2 | 2.5 | 1 | — | 4.5 | 3 | 5 | 4 | 4 | 2 | 4 | 4 | 2 | 1 | 1 |
| | | — | 2 | 2 | — | 2 | 2 | — | 3.5 | 2.5 | 5 | 5 | 5 | 2 | 2 | 2 | 1.5 | 1.5 | 2 |
| | 8 | 2 | 1 | 1 | 2 | 3 | 1 | 2 | 2 | 1 | 4.5 | 4.5 | 5 | 2.4 | 2.5 | 1 | — | — | 1 |
| | | — | 1.5 | 2 | — | 3 | 2 | — | 3 | 2.5 | 3 | 3 | — | 2 | 2 | 2 | — | 2 | 4 |
| | Average | 2.2 | 2.1 | 1.9 | 2.3 | 2.2 | 2.0 | 3.2 | 3.6 | 2.8 | 3.9 | 3.1 | 2.5 | 2.5 | 2.4 | 2.4 | 2.2 | 2.0 | 2.0 |

| | | CONTROLS | | | | | | | | | | | | | | | | | | | |
|---|---|---|---|---|---|---|---|---|---|---|---|---|---|---|---|---|---|---|---|---|---|
| | | E | | | F | | | G | | | H | | | I | | | J | | | K | | |
| | 1 | 3 | — | 3 | 4 | 3 | 1 | 3 | 3 | 3 | 4 | 3 | 4 | 3 | 4 | 5 | 2 | 3 | 3 | 3 | 2.5 | 3 |
| | | — | 4 | 4 | 4 | 2 | 2 | — | 3.5 | 4 | — | 2 | 3 | — | 4 | 3 | — | 2 | 2 | — | 2 | 4 |
| | 2 | 2.5 | 3 | 1 | 4 | 3 | 3 | 2 | 4 | 1 | 3.5 | 2.5 | 1 | 3.5 | 5 | 3 | 2 | 4.5 | 3 | 2 | 3 | 1 |
| | | — | — | — | 4.5 | 2 | 2 | — | 4 | 4 | — | 2 | 4 | — | 2.5 | 2 | — | 2 | 2 | — | 1 | 1 |
| | 3 | 5 | — | — | 3 | — | 1 | 4 | 2.5 | 1 | 3.5 | 3 | 1 | 2 | 1 | 1 | 2 | 2.5 | 3 | 3.5 | 3 | 1 |

TABLE 2-continued

| | | | | | | | | | | | | | | | | | | | | | |
|---|---|---|---|---|---|---|---|---|---|---|---|---|---|---|---|---|---|---|---|---|---|
| SUB- | 4 | 3 | 3 | 1 | 3.5 | — | 4 | 3 | 3 | 3 | 4.5 | 4.5 | 4.5 | 3.5 | 2.5 | 1 | 2 | 3 | 3 | 2.5 | 2.5 | 1 |
| | | 2.5 | 3 | 4 | — | 1 | 2 | — | 2 | 3 | 5 | 5 | 5 | — | 2 | 2 | — | — | 2.5 | — | 2.5 | 2 |
| JECT | 5 | 3 | — | 1 | 3 | — | 3 | 2.5 | 3 | — | 2.5 | 2.5 | 4 | 2 | 1 | *1 | 2 | 3 | 4 | 2 | 3 | 3 |
| | | 3 | 2 | 2 | 2 | 2 | 2 | — | 2 | 2 | — | 2 | 2 | — | 3.5 | 2 | — | 2 | 3 | — | 2 | 2 |
| | 6 | — | 3 | 3 | 3 | 4 | 3 | 3.5 | 2 | 3 | 3:5 | 3 | 1 | 2 | 1 | 3 | 2 | 2 | 4 | 2.5 | 3.5 | 2 |
| | | — | 2 | 2 | 2 | 2 | — | 2 | 2 | 5 | 2 | 2 | — | 2 | 3 | — | 2 | 4 | — | 1 | 3 |
| | 7 | 3 | 3 | — | 3.5 | 3.5 | 1 | 4 | — | 4 | 2.5 | 2.5 | 1 | 4 | 2 | 1 | 2 | 3 | 4 | 2 | 3 | 3 |
| | | — | 5 | 2 | 4.5 | 2.5 | — | — | 2 | 2 | — | 2 | 2 | — | 1 | 3 | — | 2 | 2 | — | 2 | 2.5 |
| | 8 | 3.5 | — | 3 | 3.5 | — | 1 | 4 | 4 | 2 | 3.5 | 3 | 1 | 4 | 3.5 | 4 | 3.5 | 3.5 | 3 | 3.5 | 4 | 3 |
| | | — | 5 | 5 | 4.5 | — | 4 | 4.5 | — | 4 | — | 2 | 5 | — | 4.5 | 2 | — | 4 | 4 | — | 4 | 2 |
| | Average | 3.4 | 3.3 | 2.7 | 3.5 | 2.3 | 2.2 | 3.6 | 2.8 | 2.7 | 3.8 | 2.9 | 2.7 | 3.0 | 2.5 | 2.2 | 2.2 | 2.8 | 3.0 | 2.9 | 2.7 | 2.2 |

*Color slightly changed

EXAMPLE 9

Tests were conducted to demonstrate that charged polypeptides of the present invention are soluble at a pH greater than 4, but are partially insoluble at pH less than 4.

Casein was hydrolyzed with trypsin catalysis at a pH of 8 to a molecular weight between 700 and 1600. A portion of the resultant product was centrifuged at 5,000 g at room temperature with hardly any precipitate resulting. Another portion of the product was treated by reducing the pH to 3.8 with hydrochloric acid, and then centrifuging at 5,000 g at room temperature. The resulting precipitate was redissolved at a pH of 5, and then the pH was increased to 7. The pH of the supernatant was also increased to 7.

The supernatant and redissolved precipitate were analyzed for their lysine and arginine content by a carboxypeptidase B method. This was effected by weighing samples to the nearest 0.1 mg and preparing solutions at 5.0 mg polypeptide per millimeter with 0.1 M tris acetate buffer. These solutions were incubated at 37° C. for one hour with 40 lambda of carboxypeptidase B (Worthington Biochemical Corp., 68 units per ml) after which the reaction was stopped with 0.1 ml of glacial acetic acid. Blanks were run with the substitution of water for carboxypeptidase B. Background corrections were made for lysine generation due to self-digestion of carboxypeptidase B.

The results are presented in Table 3. "Weight % percent protein" refers to how much of the protein in the portion of the product which had its pH reduced to 3.8, appeared in both the precipitate and supernatent; and "% activity" relates to the weight percent of the detected charged polypeptides appearing in the supernatant and precipitate.

The results show that a substantial portion of the polypeptides having a lysine and arginine end group present in the product prepared by trypsin catalyzed hydrolysis of casein precipitates at a pH of less than 4, i.e., 3.8.

EXAMPLES 10–13

These tests were conducted to demonstrate that charged polypeptides of the present invention are soluble at a pH of less than 9, but are partially insoluble at a pH greater than about 9.

Charged polypeptides were prepared by hydrolysis with trypsin of the four collagenous starting materials presented in Table 3. The hydrolysis was conducted at a pH of 5. A portion of the product was centrifuged at room temperature at 5,000 g with very little, if any, precipitate resulting. Another portion of the product was treated by raising the pH to 11 and then centrifuged at room temperature at 5,000 g. The resulting precipitate was redissolved at a pH of 7 and the pH of the supernatant was decreased to 7.

Carboxypeptidase tests were conducted on the redissolved precipitate and supernatant using the method of Example 9. The results are presented in Table 3. The results indicate that charged polypeptides of the present invention are partially insoluble at a pH greater than 9.

EXAMPLES 14–19

Spectroscopic analysis was conducted of raw casein (Ex. 14), the hydrolysate of Examples 9, 11, and 13. (Examples 15, 16, 17 respectively) and control treatment K of Examples 1–8 (Example 18), and Wilson X250, a commercial product believed to be prepared by hydrolysis with papain of collagen (Example 19). The results are presented in the Drawing.

TABLE 3

Effect of pH on Solubility of Charged Polypeptides

| Example No. | | Weight % Protein | (nanomole per miligram) Lysine | Arginine | % Activity |
|---|---|---|---|---|---|
| 9 | Casein tryptic hydrolysate | | | | |
| | pH 3.8 supernatant | 80 | 14.9 | 4.5 | 17 |
| | pH 3.8 precipitate | 20 | 82.6 | 15.4 | 83 |
| 10 | Bloom 225 [a] | | | | |
| | pH 11 supernatant | 97.3 | 22.1 | 118.4 | 26 |
| | pH 11 precipitate | 2.7 | 172.2 | 223.1 | 74 |
| 11 | Chrome 110 [b] | | | | |
| | pH 11 supernatant | 94.6 | 63.75 | 80.06 | 47 |
| | pH 11 precipitate | 5.4 | 62.1 | 101.2 | 53 |
| 12 | Hormel 100 [c] | | | | |
| | pH 11 supernatant | 98.2 | 23.7 | 74.17 | 40 |
| | pH 11 precipitate | 1.8 | 39.5 | 108.1 | 60 |
| 13 | Cooper 1 3/4 $_{TG}$ [d] | | | | |
| | pH supernatant | 87.5 | 4.86 | 20.48 | 10 |

TABLE 3-continued

| | Effect of pH on Solubility of Charged Polypeptides | | | |
|---|---|---|---|---|
| Example No. | Weight % Protein | (nanomole per miligram) Lysine | Arginine | % Activity |
| pH 11 precipitate | 12.5 | 87.5 | 149.4 | 90 |

[a] Keystone Gelatine Co. Dubois, Iowa
[b] Hudson Industries, 10 Hutton Ave., West Orange NJ 07052
[c] Hormel Products, 14711 E. Firestone Blvd., La Mirada, CA 90638
[d] Peter Cooper Company, Oak Creek WI Although the cosmetic preparations of this invention have been described in terms of preferred embodiments and preferred methods for using the cosmetic preparations, other embodiments of the invention are obvious to those skilled in the art. These embodiments include adding perfumes, surfactants, emollients, humectants, chelating agents such as zinc methionate, and other additives commonly used in the cosmetic industry to the cosmetic preparations. Also, polypeptides other than charged polypeptides can be added to the aqueous solution.

Because of these variation in the preferred embodiments, the spirit and scope of the appended claims should not necessarily be limited to the description of the preferred embodiments.

What is claimed:

1. A method for treating hair to improve the manageability, body and sheen thereof which comprises applying to the hair an aqueous solution having a pH from about 4 to about 7, said aqueous solution containing polypeptides, including a cosmetically effective amount of charged polypeptides, having two sterically unhindered positive charges, which charged polypeptides have the formula:

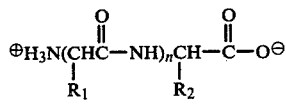

wherein n is an integer sufficient to provide a molecular weight of the polypeptide of from about 200 to about 2,000; each $R_1$ is independently a side group attached to the alpha carbon of a naturally occurring amino acid; and $R_2$ is selected from the group consisting of:

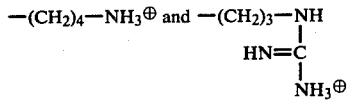

said charged polypeptides being soluble at a pH of from about 4 to about 9 and partially insoluble at a pH less than about 4 and at a pH greater than about 9, and wherein at least 16 mole percent of the polypeptides of the aqueous solution are said charged polypeptides; said polypeptides being formed by hydrolysis of proteins containing from about 12% to about 70% by weight arginine and lysine in combination by trypsin catalysis.

2. The method of claim 1 in which the aqueous solution has a pH from about 4 to about 5.

3. The method of claim 1 in which the aqueous solution is a conditioner comprising from about 3 to about 35 percent by weight polypeptides.

4. A method for treating hair to improve the manageability, body and sheen thereof which comprises applying to the hair an aqueous solution having a pH from about 4 to about 7, said aqueous solution containing polypeptides, including a cosmetically effective amount of charged polypeptides, having two sterically unhindered positive charges, which charged polypeptides have the formula:

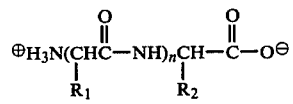

wherein n is an integer sufficient to provide a molecular weight of the polypeptide of from about 200 to about 2,000; each $R_1$ is independently a side group attached to the alpha carbon of a naturally occurring amino acid; and $R_2$ is selected from the group consisting of:

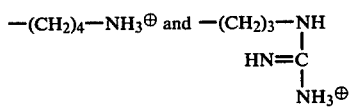

said charged polypeptides being soluble at a pH of from about 4 to about 9 and partially insoluble at a pH less than about 4 and at a pH greater than about 9, and wherein at least 16 mole percent of the polypeptides of the aqueous solution are said charged polypeptides; said polypeptides being formed by hydrolyzing with trypsin, a gelatin comprising of from about 12 to about 70 percent by weight arginine and lysine in combination.

5. The method of claim 4 wherein the aqueous solution has a pH from about 4 to about 5.

6. The method of claim 4 in which the aqueous solution is a conditioner comprising from about 3 to about 35 percent by weight polypeptides.

* * * * *